US006833460B2

(12) United States Patent
Anderson

(10) Patent No.: US 6,833,460 B2
(45) Date of Patent: Dec. 21, 2004

(54) PREPARATION AND USE OF GAMMA-BUTYROLACTONES AS CROSS-LINKING AGENTS

(75) Inventor: Albert Gordon Anderson, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/997,667

(22) Filed: Nov. 28, 2001

(65) Prior Publication Data

US 2002/0183528 A1 Dec. 5, 2002

Related U.S. Application Data

(63) Continuation-in-part of application No. 09/591,452, filed on Jun. 12, 2000, now Pat. No. 6,423,850.
(60) Provisional application No. 60/139,940, filed on Jun. 18, 1999.

(51) Int. Cl.$^7$ ..................... C07D 32/00; C07D 305/12; C08G 63/02; C09K 3/00
(52) U.S. Cl. ..................... 549/200; 549/320; 549/323; 528/192; 528/354; 528/415; 252/182.33
(58) Field of Search ................................. 549/200, 320, 549/323; 252/182.23; 528/354, 192, 415

(56) References Cited

U.S. PATENT DOCUMENTS

| 2,768,148 | A  |   | 10/1956 | Schildknecht et al. |         |
|-----------|----|---|---------|---------------------|---------|
| 3,429,851 | A  |   | 2/1969  | Coates et al.       |         |
| 3,678,167 | A  |   | 7/1972  | Ghosh et al.        |         |
| 4,898,977 | A  |   | 2/1990  | Herold et al.       |         |
| 5,010,189 | A  |   | 4/1991  | Herold et al.       |         |
| 5,606,078 | A  |   | 2/1997  | Goschke et al.      |         |
| 5,705,658 | A  |   | 1/1998  | Goschke et al.      |         |
| 6,258,895 | B1 |   | 7/2001  | Hocker et al.       |         |
| 6,346,599 | B1 | * | 2/2002  | Goldberg et al.     | 528/354 |
| 6,423,850 | B1 | * | 7/2002  | Anderson            | 549/200 |

FOREIGN PATENT DOCUMENTS

| EP | 0174866 B1 | 3/1993  |
|----|------------|---------|
| GB | 1140721    | 1/1969  |
| WO | WO 00 78743 | 12/2000 |

OTHER PUBLICATIONS

Copy International Search Report (PCT/US 02/41452) dated Oct. 10, 2003.
Rosowsky, Chemical Abstracts, Columbus Ohio, vol. 66, Feb. 13, 1967, No. 7.
Bensel et al.—Preparation of Bi(alpha–methylene–gamma–lactones) Institute for Organic Chemistry, Liebigs Ann Chem., 1977, 1572–1584.
Hayashi et al., Studies on Antitumor Substances XII Synthesis of Bis(2,3–epoxypropyl)amine Derivatives and the Reaction with Some Nucleophiles, Chem. Pharm Bull., 19(10)2003–2008 (1971).
Hansch et al. A Survey of Hammett Substituent Constants and Resonance and Field Parameters, Chem. Rev. 1991, 91, 165–195.
Stock, The Origin of the Inductive Effect, *Journal of Chemical Education*, 49/6, 400–404, 1972.
Hosie et al., Failure of the Antiperiplanar Lone Pair Hypothesis in Glycoside Hydrolysis, Synthesis, Conformation and Hydrolysis of α–D–xylopyranosyl–and α–D–glucopyranosyl–pyridinium salts, *J. Chem. Soc. Perkin Trans.*, 1121–1131, 1983.
H. E. Hogberg et al., Synthesis and gas chromatographic separation of the eight stereoisomers of diprionol and their acetates, components of the sex pheromone of pine sawfiles, Tetrahedron, 1990, 3007–3018, 46 (8).
Effects of Structure on Reactivity, Advanced Organic Chemistry: Reactions Mechanisms and Structures, *J. Wiley and Sons, NY*, 278–286, 1992.
Lehmann, J. et al., 42210, Journal: CHBEAM; Chem. Ber.: GE; 107; 1974.
Ya, Y. et al., 45876; Journal; CHCCAL; Chem. Heterocycl. Compd. (Engl. Trans.); EN; 7; 1971.
Gonzalez, A., 5581994; Journal; SYNCAV; Synth. Commun.; EN; 21; 5; 1991.
Lehmann, J., 5749722; Journal; ARPMAS; Arch. Pharm. (Weinheim Ger.); GE; 317; 5; 1984.
Yamasaki, T. et al., 6066955; Journal; HTCYAM; Hetrocycles; EN; 43; 8; 1996.
C. Melchiorre et al., Molecular requirements at the cholinergic receptors. Importance of ether oxygens in the dioxoiane series, Eur. J. Med. Chem.—Chimica Therapeutics, 1978, 357–361, 13 (4).

* cited by examiner

*Primary Examiner*—Deborah C. Lambkin
(74) *Attorney, Agent, or Firm*—Steven C. Benjamin; Linda K. H. Sauerbrunn

(57) ABSTRACT

The rate of aminolysis of butyrolactones is predictably adjusted by attaching a substituent having a known field effect value (F) to the alpha position before reacting the substituted buytrolactone with an amine. The aminolysis product is a gamma-hydroxy amide. The resulting materials are useful as the cross-linking agents in a variety of coatings and coatings processes.

13 Claims, 1 Drawing Sheet

PREPARATION AND USE OF GAMMA-BUTYROLACTONES AS CROSS-LINKING AGENTS

FIELD OF THE INVENTION

This invention relates to the preparation of gamma-butyrolactones and their use as cross-linking agents in various processes, including coating applications. Gamma-butyrolactones as cross-linking agents impart favorable properties to coating materials, do not pose serious health risks in commonly used coating processes, and therefore are suitable alternatives for isocyanates in coating compositions and application processes.

TECHNICAL BACKGROUND OF THE INVENTION

Materials commonly used for coatings, particularly those used in the automotive industry, utilize isocyanate compounds in coating formulations due to cross-linking properties of the compounds. Diisocyanate compounds react slowly at room temperature with amines and aliphatic alcohols to make polymers having urethane or urea crosslinks. Isocyanates may also cross-link with amines or alcohols during a baking step of the coating process and result in urethane or urea crosslinked polymers. Both urethanes and ureas are known to impart desirable properties in coating materials. Polymer backbones appended with hydroxyl groups or amine groups harden coating materials such as paint.

Isocyanates are volatile compounds. During the coating or baking step, persons working in the automotive industry, for example, are exposed to the vapors. Concern about the potential toxicity and health related effects associated with isocyanates suggests that alternatives are needed. The present invention discloses alternatives to isocyanates as cross-linking agents.

SUMMARY OF THE INVENTION

Disclosed in this invention is a lactone composition, as represented in structure I, wherein each n is independently 1 to 3; L is either present as a substituent having two functional groups, or is a direct bond forming a spiro-butyrolactone, or is H wherein rings of the structure are not connected, or is a radically polymerizable group wherein the rings of the structure are not connected; Y is either present independently as alkyl, alkenyl, alkynyl, aryl or a direct bond; each X is independently a substituent having a field effect, F, between −0.42 and +1.58

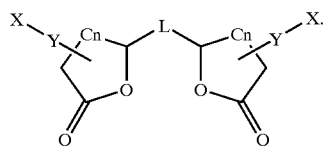

I

Also disclosed in this invention is a process comprising contacting lactones of structure B with an amine to form a hydroxy amide, wherein each Y is present independently as alkyl, alkenyl, alkynyl, aryl, or a direct bond; each X is independently a substituent having a field effect, F, between −0.42 and +1.58; wherein R is a branched or straight chain alkyl group of $C_1$ to $C_{10}$, or an aryl group; and wherein each n is independently 1 to 3.

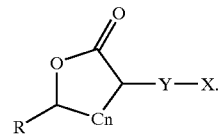

"B"

This invention also discloses a process comprising contacting a spiro-bislactone of structure A, wherein each n=1 to 3 independently and R is a branched or straight chain alkyl group of $C_1$ to $C_{10}$, or an aryl group; with an amine to form a hydroxy amide.

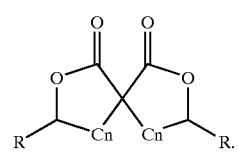

"A"

Also disclosed in a process comprising contacting a bicyclo-lactone of structure C wherein R is a branched or straight chain alkyl group of $C_1$ to $C_{10}$, an aryl group; or C(O)OE wherein E is independently alkyl or aryl, with an amine.

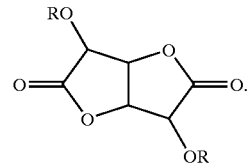

"C"

Also disclosed in this invention is a process comprising contacting a polymer comprising at least one polymerized lactone monomer of structure D with an amine to form a hydroxy amide, wherein each Y is present independently as alkyl, alkenyl, alkynyl, aryl, or a direct bond; each X is independently a substituent having a field effect, F, between −0.42 and +1.58; and wherein $R_{PG}$ is a radically polymerizable substituent group selected from the group consisting of styrene, acrylate, methacrylate, acrylamide, and methacrylamide; and wherein n is independently 1 to 3.

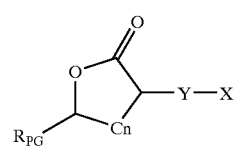

"D"

Still another disclosure of this invention is a process, comprising:
(i) performing the steps of any one of the disclosed processes; and applying a product resulting from step (i) to an object surface.

Also disclosed is an article treated by a process disclosed as described above.

DETAILED DESCRIPTION OF THE INVENTION

Figure 1:
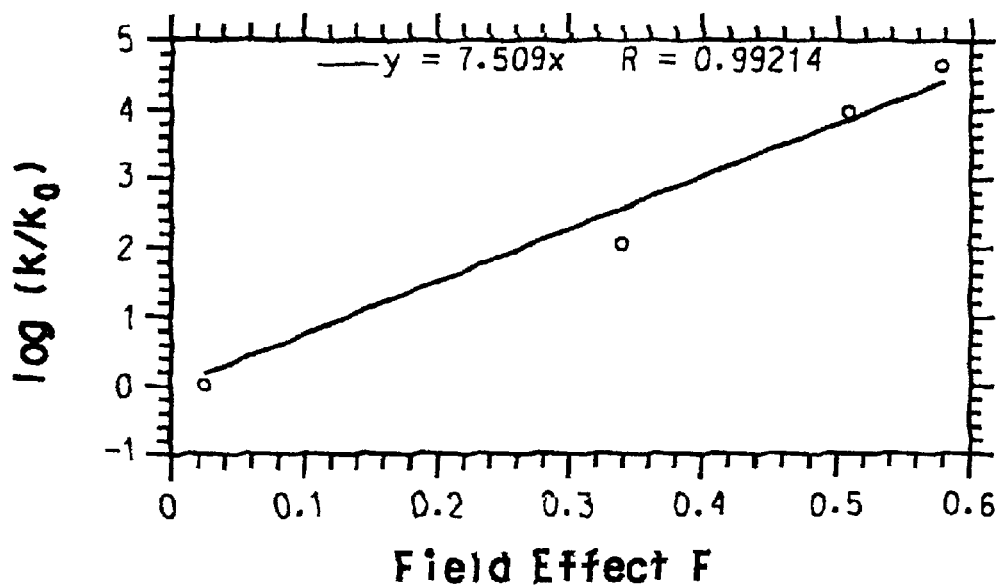
FIG. 1 is a plot of the relative aminolysis rates, expressed as $\log(k/k_o)$, for the substituted gamma-butyrolactones versus the F values for the functional groups as given in Hansch, et al., Chem. Rev., 1991, 91, pp. 165–195. The x axis is labeled "F". The letter "F" refers to the substituent constant that is related to the "field effect".
Figure 2:
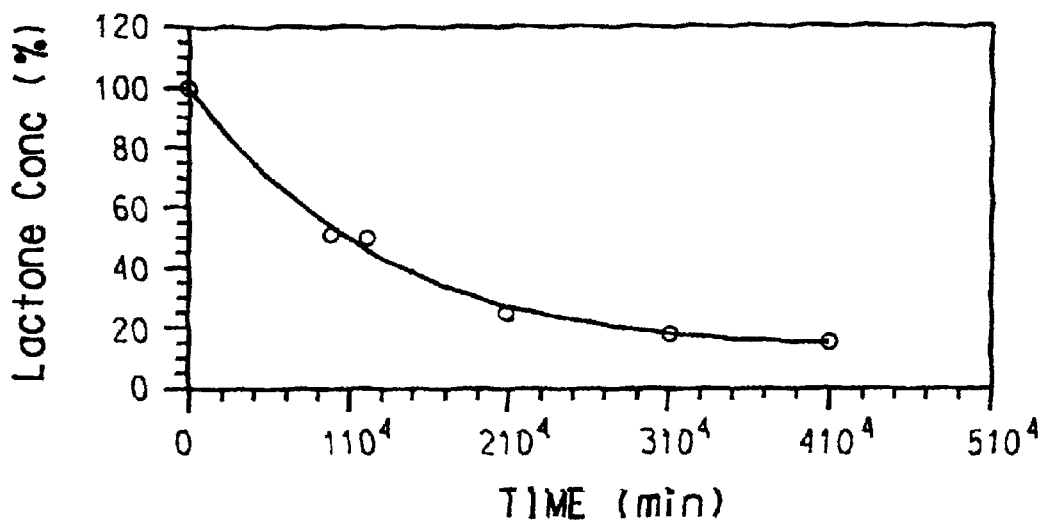
FIG. 2 is a plot depicting the aminolysis rate of gamma-butyrolactone.

Isocyanates are used extensively in materials used as coatings. One example of isocyanate use is in the automotive industry. Isocyanates are used as cross-linking agents for coating automobiles during different manufacturing coating processes. Concern has increased over the potential health hazards associated with the use of isocyanates. This present invention discloses alternatives to coating formulations comprising isocyanates and alternatives to the use of isocyanate formulations in coating processes, including electrocoat (E-coat), original equipment manufacturing (OEM), and Refinish.

The aminolysis of gamma-butyrolactones may be described as an amide forming reaction caused by the reaction of a primary amine with a cyclic ester, or lactone, to give a hydroxyamide. Lactones do not always react with amines quickly enough for application as a cross-linking agent in some coating processes. When the aminolysis reaction proceeds too slowly, the curing of the material is time consuming. For room temperature curing, a reaction that proceeds too slowly is industrially inefficient. An increased aminolysis reaction rate at or about room temperature produces a crosslinking agent which is useful for clear coats and color coats. Such processes are used in automotive body repair shops (i.e., Refinish), for example, where baking the finish is impractical. However, for applications where baking is required, if the aminolysis reaction rate is increased too sharply, the accelerated reaction may result in an aesthetically and mechanically undesirable coating, because the prepolymer begins to crosslink in the baking process before the coating has had enough time to flow out to form a smooth surface, thus resulting in a rough surface. These problems are resolved by the present invention.

In this invention the aminolysis rate can be predicted, thereby providing alternatives to currently used processes. This invention can be tailored to the particular coating process. An adjustable aminolysis reaction rate can result in a crosslinking agent which yields a melting and flowing of the coating material to produce a smooth and evenly coated surface when such a surface is desired.

Specifically, this invention discloses compounds and processes to predictably adjust the rate of aminolysis of gamma-butyrolactones by appending a substituent having a known field effect value (F) to the alpha position of a gamma-butyrolactone before reacting the lactone with an amine. The resulting compound of the aminolysis is a gamma hydroxy amide, which can be used as the cross-linking group in a variety of coating formulations and processes. Throughout this description, reference is made to gamma-butyrolactones. However, it should be understood that this invention is not limited to gamma-butyrolactones, but also covers delta- and epsilon-lactones, as indicated by structure I.

After many years of effort, physical organic chemists developed a number of sigma constants to apply to various aromatic and aliphatic reactions. C. G. Swain and E. C. Lupton, J. Am. Chem. Soc., 1968, 90, 4328, reanalyzed the data that was used to develop the sigma constants $\sigma_m$, $\sigma_p$, $\sigma_p^-$, $\sigma_p^+$, $\sigma_I$, $\sigma_R^o$ and found that the sigma constants were not independent. The sigma constants contained contributions from both resonance and field contributions. It was discovered that a linear combination of two sets of new values "F" (which expresses the field-effect contribution of a functional group) and "R" (which measures the resonance contribution of the same group) satisfactorily expressed 43 sets of σ values. Each set was expressed as $$\sigma = fF + rR$$

where "f" and "r" are weighting factors. The importance of the expression is that the electronic effects of a given substituent could be separated and expressed as only two constants. A useful set of F and R values is given in C. Hansch, et al., Chem. Rev., 1991, 91, pp. 165–195, herein incorporated by reference.

Having derived a universal set of F and R constants for substituent groups, these can then be used in a Hammett equation to examine the effect of a particular substituent on the reaction rate of a particular reaction. In general, the Hammett equation can be written as $$\text{Log } (k/k_o) = \rho F + \rho R$$

where $(k/k_o)$ is the relative reaction rate, $\rho$ is rho, and F and R are the field and resonance contributions of the substituent groups. The slope of the line, called rho, is given the Greek symbol, $\rho$, and represents the sensitivity of the reaction to the variation of substituents. (An explanation of the use of Hammett equations can be found in J. March, "Advanced Organic Chemistry", 3rd ed., John Wiley & Sons, Inc., N.Y., 1985, pp 242–250 and references cited therein, and is herein incorporated by reference.) In order to use the Hammett equation to predict the relative reaction rates of lactones, it was first necessary to establish that the Hammett equation applies to aminolysis of lactones. For aliphatic lactone rings, only the field effect should apply since the resonance effect is absent in compounds that do not have conjugated double bonds joining the substituent with the reaction center. In this case, the reaction center is the lactone carbonyl group. Since resonance contributions to the aminolysis reaction of a saturated lactone are absent, the Hammett equation given above can be modified to give $$\text{Log } (k/k_o) = \rho F$$

The relative aminolysis reaction rate for a lactone possessing a given substituent was plotted against the F value for the given substituent. If the Hammett equation applies, the resulting set of points should form a straight line that passes through the origin [0,0]. The relative reaction rate for various lactones was plotted against F and is shown in FIG. 1. The resulting points were fitted to a straight line using a linear least squares equation. The resulting line has a correlation coefficient of 0.992. It was not known beforehand whether lactones would obey the Hammett equation. From this novel result, it can be concluded that the Hammett equation can be used to relate and predict the effect of an alpha substituent on the aminolysis reaction rate of a cyclic lactone. Using such a high correlation coefficient, our invention utilizes an understanding of how to substitute a lactone, having 3 to 6 members in the lactone ring, to give any reaction rate desired. One can speed up or slow down the aminolysis reaction at will by the choice of substituents.

From FIG. 1 it can be seen that the relative reaction rates vary by almost five orders of magnitude. It is experimentally difficult to employ uniform reaction conditions when such large differences in relative reaction rate are found. On some of the fastest reacting lactones, the concentration of the reactants had to be reduced by half in order to determine their reaction rates. The rates were then adjusted to account for the effect of dilution. The adjustment is based on aminolysis studies performed on acyclic esters; in these studies, the reaction rate was found to obey the rate law Rate $(R)=k_1[\text{amine}]^2[\text{ester}]+k_2[\text{amine}][\text{ester}]$ (See F. M. Menger and J. H. Smith, J. Am. Chem. Soc., 1972, 94(11), 3824–3829). The dominant term in this expression is the second one since the magnitude of the rates $k_1$ and $k_2$ are approximately equal; this means that the observed reaction rate will be increased by a factor of 4.0 when the concentration of both amine and lactone are reduced by half. The rate law for lactones is similar to those for esters. The relative reaction rate can then be adjusted by the inverse of 4.0, i.e., 0.25, to compare the reaction rates of the diluted lactones with lactones that have not been diluted.

In the aminolysis of lactones, the reaction rate was not determined directly. What was determined was the half-life of the reaction, $t_{1/2}$, which is the point in time when the concentration of lactone or amine becomes equal to the concentration of hydroxyamide. For a second order reaction $t_{12A}=1/(k[A])$, where [A] is the concentration of lactone A and k is the reaction rate. Thus $k=1/(t_{1/2}[A])$. Similarly, the reaction rate for the standard, $k_o$, is $k_o=1/(t_{1/2}[B])$. When the half-life of lactone A is compared to the half-life of a standard lactone, B, it is seen that the ratio of reaction rates is inversely porportional to the ratio of half-lives (see C. Capellos and B. H. J. Bielski, "Kinetic Systems", Wiley-Interscience, NY, 1972, p 4).

$(k/k_o)=(1/(t_{1/2}[A]))/((1/(t_{1/2}[B]))=t_{1/2B}/t_{1/2A}$

These adjusted reaction rates are exemplified and depicted graphically in the plot of FIG. 1. Equal quantities of N-butylamine and substituted lactone were allowed to react at room temperature (22° C.) in an NMR tube. The integrated intensity of the $CH_2$ adjacent to the amide nitrogen in butyl amine and the $CH_2$ of the resulting hydroxyamide was measured by $^1H$ NMR. The integrated intensity was plotted against time and the time when the curves crossed was taken as the half-life of the reaction, since at that time both species (amide and butylamine) were equal in concentration. Since all concentrations of reactants were kept the same, the relative rates ($k/k_o$) are proportional to the relative crossover times.

The relative "F" values provide predictable information about the aminolysis reaction rate for those substituents where F equals from about –0.42 to about +1.58, which applies to more than 500 substituents. Various electron withdrawing groups, which have an F value greater than 0.03, and which are appended to the alpha position of the lactone carbonyl group give "activated" lactones. By "activated" is meant a lactone having electron withdrawing properties. Various electron withdrawing groups may be used, including —CN and —C(O)COR. Lactones having these substituents have different reaction rates. The electron withdrawing groups can be classified by their F values. Positive F values indicate electron withdrawing properties and negative F values indicate electron donating properties. H is assigned an F value of 0.03. The F value of a group is related to the half-life of the reaction of lactones with amines. For example, the adjusted half-lives of —CN, —C(O)COR and —H are about 1.25 minutes, about 88 minutes and about 165 hours, respectively.

In an embodiment of this invention, the substituted gamma-butyrolactone has the structure:

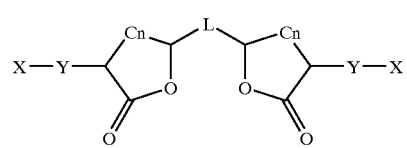

I wherein each n is independently 1 to 3; L is a bifunctional compound or nothing; each Y is independently nothing, alkenyl, alkynyl, or aryl; each X is independently a substituent having a field effect, F, between –0.42 and +1.58; wherein when Y is nothing, then X is appended directly to the lactone ring; wherein when L is hydrogen, the lactone rings are not connected; and wherein when L is nothing, the lactones form a spiro-bislactone (See Fig. A below). When Y is alkenyl, the alkenyl group is defined as

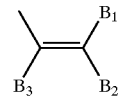

wherein each $B_1$ to $B_3$ is individually a substituent group X as defined above.
When Y is phenyl, the phenyl group is defined as

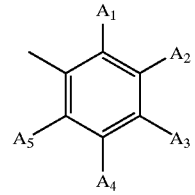

wherein $A_1$ to $A_5$ are each individually a substituent group X as defined above. When Y is an alkynyl group, it has the structure

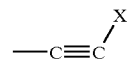

where X is as defined above.

Any primary or secondary amine with a reactive amino group is suitable for this process. Primary amines are preferred.

During this reaction the lactone rings opens and a gamma-hydroxy amide is formed. For example, where —CN is the activating group on the lactone, the reaction can be depicted as

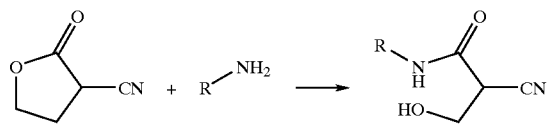

This invention discloses the use of spiro (A), substituted (B) and bicyclic (C) lactones of the following structures, as well as the use of polymers, such as acrylic polymers, containing lactone group(s) prepared from lactone monomers (D) of the structure reported below

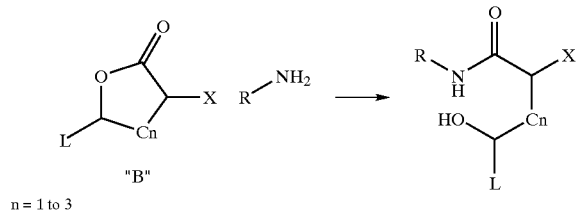

"B"

n = 1 to 3

The bicyclolactone can have a structure such as

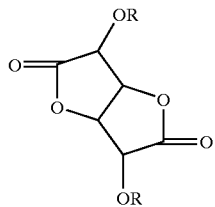

"C"

and the spirolactone can have a structure such as

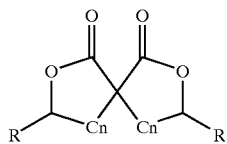

"A"

and the lactone monomer can have the structure

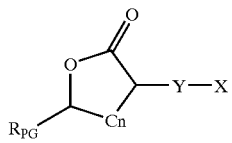

"D"

for use as cross-linking agents in coating processes, wherein the linking group, $C_n$, is defined for when n=1 to 3, preferably n=1 to 2 and most preferably n=1. The F values for substituent X and reaction temperatures permits customization of the reaction for the coating process by predicting the aminolysis rates of the cross-linking agent. In one embodiment of this invention bis-lactone is reacted with an amine. In another embodiment of this invention a monolactone is reacted with a diamine or an aminoalcohol. The substituents which are useful to activate the lactone disclosed in this invention are functional groups having an F value from about –0.42 to about 1.58 and are provided in Table 1.

The preferred substituents, X, are found in Table 1, identified with the numbers 2, 5, 15, 28, 30, 32, 33, 34, 35, 37, 40, 43, 45, 47, 48, 49, 58, 62, 70, 74, 75, 76, 77, 78, 80, 84, 85, 90, 93, 94.95, 97, 98, 99.100, 101, 102, 103, 111, 112, 113, 114, 115, 116, 117, 118, 119, 120, 122, 125, 127, 128, 133, 139, 141, 142, 143, 144, 148, 150, 151, 153, 156, 160, 161, 162, 163, 165, 166, 167, 168, 169, 175, 177, 178, 179, 185, 186, 187, 188, 189, 191, 192, 193, 194, 195, 197, 198, 199.200, 201, 202, 203, 204, 205, 206, 207, 208, 209, 210, 211, 212, 213, 214, 215, 216, 217, 219, 221, 222, 223, 224, 225, 231, 232, 233, 234, 238, 239, 240, 241, 242, 243, 244, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 283, 284, 285, 286, 288, 289, 291, 292, 293, 294, 295, 297, 298, 300, 301, 302, 303, 304, 305, 306, 307, 308, 314, 315, 316, 317, 318, 319, 320, 321, 322, 323, 324, 325, 326, 327, 328, 329, 331, 332, 333, 334, 335, 336, 337, 338, 339, 340, 341, 342, 343, 344, 345, 346, 348, 349, 350, 351, 352, 353, 354, 355, 356, 357, 358, 359, 360, 361, 362, 363, 364, 365, 366, 367, 368, 369, 370, 371, 375, 376, 377, 378, 379, 380, 381, 382, 383, 384, 385, 386, 387, 388, 389, 390, 391, 392, 393, 394, 395, 396, 397, 398, 399, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 453, 454, 455, 456, 457, 458, 459, 460, 461, 462, 463, 464, 465, 466, 467, 468, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510511, 512, 513, 514, 515, 516, 517, 518, 519, 520, 521, 522, 523, 524, 525, 526, 527, 528, 529 and 530.

The most preferred substituents, X, are found in Table 1, identified with the numbers 2, 5, 15, 28, 32, 33, 40, 45, 49, 70, 75, 76, 78, 80, 84, 85, 90, 93, 99, 100, 101, 102, 103, 111, 117, 118, 119, 120, 122, 125, 127, 128, 133, 139, 141, 142, 143, 144, 148, 150, 151, 153, 156, 160, 161, 162, 165, 166, 167, 168, 169, 175, 177, 178, 179, 185, 186, 187, 188, 189, 191, 192, 193, 194, 194, 198, 199, 200, 201, 202, 203, 207, 210, 211, 212, 213, 214, 215, 216, 217, 219, 221, 222, 223, 224, 225, 231, 232, 233, 234, 238, 239, 240, 241, 250, 251, 252, 253, 254, 267, 270, 271, 272, 273, 275, 276, 277, 278, 279, 285, 291, 292, 293, 294, 295, 297, 298, 300, 303, 317, 318, 323, 325, 332, 333, 334, 335, 336, 337, 345, 378, 379, 380, 384, 388, 395, 396, 403, 404, 405, 406, 407, 408, 409, 410, 411, 416, 417, 420, 424, 425, 433, 448, 449, 450, 453, 458, 460, 474, 475 and 512.

Temperatures of the process is not critical, a preferred temperature range for ambient (Refinish) curing is about –20° C. to about 120° C., more preferably about 0° C. to about 110° C., and especially preferably about 10° C. to about 100° C. Preferred temperatures for E-coat or OEM applications are not critical, a preferred temperature being in the range of 20° C. to about 250° C., more preferably about 40° C. to 220° C., most preferably about 100° C. to 200° C. Ratios of reactants are not critical, but in order to most efficiently utilize the ingredients a molar ratio of about 1:1 for the lactone and primary amine groups is preferred.

In general, all that is necessary for the reaction to occur is to bring the reactants into contact, as in solution, or if one or both of the primary amine and lactone are liquids, without solvent, for a period of time sufficient to carry out the reaction.

Polymers that contain lactone groups are especially useful since they may be crosslinked by multifunctional compounds that can react with lactone groups. Multifunctional amines are particularly desirable in this respect, since upon reaction with the lactone, hydroxyamides are formed. This invention discloses that butyrolactones are desirable in polymers for certain uses; for example, in coatings butyrolactones impart certain improved properties such as gloss, impact resistance, adhesion and toughness.

The gamma-butyrolactones can be introduced into polymers by being part of polymerizable monomers, such as those described above, which may be prepared by the methods reported in Zamzow et al U.S. Pat. No. 6,258,895 issued Jul. 10, 2001 and Noe et al, Monatsh. Chem. (1997) 128(5), 509–527, and which may be free-radically copolymerized with other monomers to form a copolymer which may be crosslinked with a di- (or higher) functional primary amine or a primary amine-containing polymer. Such a lactone containing polymer preferably contains an average of 2 or more lactone groups per polymer molecule. Conversely, a polymer containing primary amine groups may be crosslinked by a compound containing two or more lactone groups or a polymer containing lactone groups. In both instances, the crosslinks contain desirable hydroxyamide groups. In a coating process, the lactone may be premixed with either the polymer or crosslinking compound, and then the polymer and crosslinking compound mixed with each other, and the polymer will eventually crosslink. If meant for a coating, the mixture may be applied to the surface of an object in a normal manner (e.g., spraying, dipping or brushing) and upon standing at ambient conditions the polymeric coating will crosslink. Other ingredients normally present in such coatings can also be present, such as pigments, dyes, antioxidants, reflective agents, dispersants, etc.

Coatings which are crosslinked by the process described herein are especially useful for transportation vehicles such as airplanes, automobiles, trucks and railroad cars. They are especially suitable for refinish operations, i.e., repainting of a surface after the coated object has been in us or service for some time period. The coatings may be applied without the need for baking, as is often done when the transportation vehicle is first manufactured.

EXAMPLES

Unless otherwise stated, all chemicals and reagents were used as received from Aldrich Chemical Co., Milwaukee, Wis.

$^1$H NMR spectra were recorded on a GE Omega 300 spectrometer (General Electric Co., Schenectady, N.Y.) operating at 300.275 MHz, relative to a tetramethylsilane internal standard, and are given in ppm. Durene was used as an inert internal standard.

Infrared spectra were recorded on a Nicolet Impact 410 spectrometer manufactured by Nicolet Instrument Corp., Doylestown, Pa.

Synthesis of Substituted Gamma-Butyrolactones

Example 1

Synthesis of 3-cyano-5-phenoxymethyl-gamma-butyrolactone

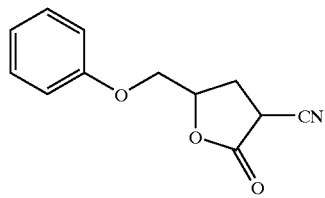

A 4-necked 500 ml round bottomed flask equipped with a nitrogen bubbler, reflux condenser, and stirrer was charged with 250 ml of ethanol. Over a period of 10 minutes 2.4 g of sodium hydride was added with stirring. After stirring., a solution of 3.3 g of malononitrile in 10 ml of ethanol was added. To this mixture was added during 15 min. a solution of 7.5 g 1,2-epoxy-3-phenoxypropane from an addition funnel. The reaction mixture was refluxed for 2 hours and then allowed to stand overnight at room temperature. The solvent was removed on a rotary evaporator and the residual syrup was dissolved in 250 ml of methylene chloride and reacted with 250 ml of 1 N hydrochloric acid for 30 min. The methylene chloride layer was separated and the water layer was washed with 25 ml of methylene chloride. The methylene chloride layers were combined, washed with 200 ml of water, and dried over magnesium sulfate. The solvent was removed. The residue was dissolved in ethanol, treated with charcoal, and filtered. The filtrate gave 3.6 g of white crystals mp 125–130° C. IR (nujol) 1785.66 and 1772.54 cm$^{-1}$ (cis and trans isomers of lactone carbonyl). $^1$H NMR (acetone-d$_6$) 5.1 and 5.2 ppm (both m, cis and trans isomers of 5-H lactone ring).

Example 2

Synthesis of 5.5'-[1,4-butylenebis(oxymethylene)]-bis[ethyl(tetrahydro-2-oxo)-3-furancarboxylate

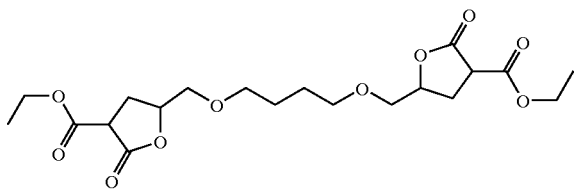

A 2 liter 4-necked round bottomed flask equipped with a mechanical stirrer, reflux condenser, nitrogen bubbler and thermocouple thermometer was charged with 600 ml ethanol and 58.08 g of sodium methoxide. Then, while stirring, 168.2 g of diethyl malonate was added followed by 101.1 g of 1,4-butanedioldiglycidyl ether. The reaction was refluxed for one hour. The reaction was neutralized with 5% hydrochloric acid and extracted four times with 250 ml of methylene chloride. The methylene chloride layers were combined and washed with 100 ml water, separated, dried over magnesium sulfate, filtered, and concentrated to give a syrup. IR (neat) 1780.64 and 1731.25 cm$^{-1}$ (cis and trans lactone isomers). $^1$H NMR (CDCl$_3$) 4.7 and 4.8 ppm (both m, cis and trans isomers of 5-H lactone ring).

Example 3

Synthesis of 3-benzenesulfonyl-5-methyleneoxybutyl-butyrolactone

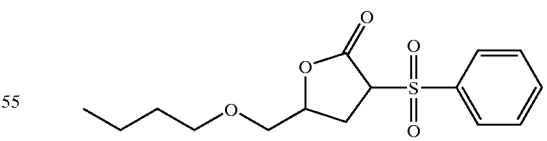

A vial was charged with 3 g of methyl phenylsulphonylacetate, 3 g of THF, and 1.62 g of sodium ethoxide. To this mixture was added 0.65 g of butyl glycidyl ether. The vial was placed under a pressure of 150 psig of nitrogen (to retard evaporation of the solvent) and heated at 100° C. for four hours. The vial was cooled, depressurized, and the contents mixed with 1 ml of conc. hydrochloric acid and 2 ml of chloroform. The mixture was washed twice with 5 ml of water, separated, dried over magnesium sulfate, treated with charcoal, filtered, and the solvent removed on the rotary evaporator to give a syrup. IR (neat) 1778.92 and 1743.69 cm$^{-1}$(cis and trans lactone isomers). $^1$H NMR (CDCl$_3$) 4.6 and 4.75 ppm (both m, cis and trans isomers of 5-H lactone ring).

Example 4

Synthesis of (1-Methylethylidene)bis(4,1-phenyleneoxymethylene)-bis[5-(3-carboethoxyfuran-2-one)]

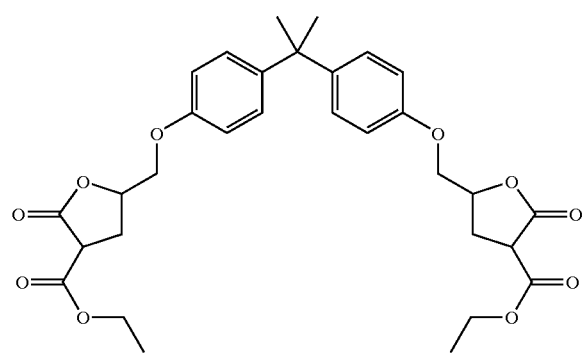

A pressure vessel was charged with 5.05 g of diethyl malonate, 9.5 g of ethanol, and 10.5 g of sodium ethoxide. To this mixture was added 5.1 g of bisphenol-A diglycidyl ether. The bomb was sealed, pressured with 150 psig with nitrogen and then heated to 100° C. for two hours. The bomb was cooled, depressurized, and the product neutralized with conc. hydrochloric acid. The product was taken up in chloroform, washed with water, dried over magnesium sulfate, filtered, and the solvent removed to give 6.6 g (80% yield) of resinous product. By proton NMR, all the epoxy groups had been converted to product IR (neat) 1780.88 (lactone carbonyl), 1735.92 cm$^{-1}$. $^1$H NMR (CDCl$_3$) 4.8 and 4.9 ppm (both m, cis and tans isomers of 5-H lactone ring).

Example 5

Synthesis of (1-Methylethylidene)bis(4,1-phenyleneoxymethylene)-bis[5-(3-carbomethoxyfuran-2-one)]

A similar reaction to that found in Example 4, using dimethyl malonate in place of diethyl malonate, gave the corresponding carbomethoxy derivative. Use of higher temperature for this reaction (100° C. rather than refluxing methanol) resulted in a distinctly higher yield (95% vs. 45%).

Example 6

(1-Methylethylidene)bis(4,1-phenyleneoxymethylene)bis[5-(furan-2-one)]

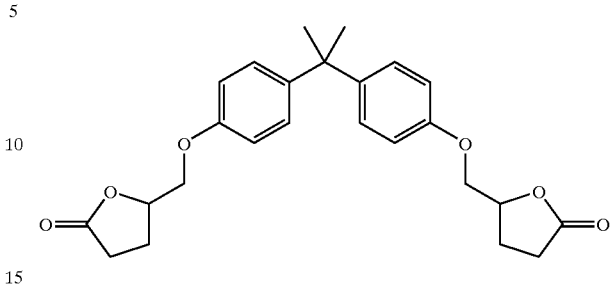

A 100 ml round bottomed flask was charged with 0.7 g of anhydrous magnesium chloride, 32 ml of dimethyl acetamide and 6 drops of water. To the flask was added 4.4 g of (1-methylethylidene)bis(4,1-phenyleneoxymethylene)bis[5-(3-carboethoxyfuran-2-one)] as synthesized in Example 4 above. After refluxing the mixture for 40 min., IR spectra revealed that the lactone carbonyl peak at 1780 cm$^{-1}$ remained and the ester carbonyl peak at 1735 cm$^{-1}$ was absent. Subsequently, it was found that heating the starting material in a vial under nitrogen pressure at 200 psig at a temperature of 150° C. using hydrochloric acid or tosic acid was also effective for complete decarboethoxylation.

Aminolysis of Gamma-Butyrolactones

The aminolysis of gamma-butyrolactones may be described as an amide forming reaction caused by the reaction of a primary amine with a lactone to give a hydroxyamide:

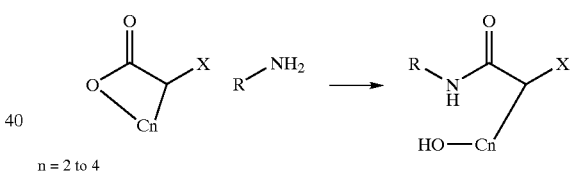

n = 2 to 4

Example 7

Aminolysis of Gamma-Butyrolactone

The aminolysis of the parent lactone, gamma-butyrolactone, was conducted in a sealed NMR tube that was held at room temperature (21° C.+/−1° C.) during the course of the experiment. The integrated intensity of two peaks was monitored. The peaks corresponded to the methylene group adjacent to the ester ring oxygen of the lactone (triplet located at 4.3 ppm) and the methylene group adjacent to the nitrogen in butyl amine (triplet located at 2.5 ppm). The ratio of ester/amine was computed and is shown as % concentration of lactone in the table below.

Example 8

Aminolysis of 3-cyano-5-phenoxymethyl-gamma-butyrolactone

A solution of 3-cyano-5-phenoxymethyl-gamma-butyrolactone (as prepared in Example 1) was prepared by weighing into a NMR tube 0.0893 g (0.0004375 mol) of 3-cyano-5-phenoxymethyl-gamma-butyrolactone and 0.0147 g of durene dissolved in 0.589 g of DMF-$d_7$. Then 0.043 ml (0.0004375 mol) of N-butylamine was added. The tube was sealed and the $^1$H NMR spectrum recorded at various times. The integrated intensity of the triplet due to the methylene group adjacent to the nitrogen atom of butylamine at 2.58 ppm (here designated "a") and the integrated intensity of the triplet due to the methylene group adjacent to the amido nitrogen at 3.18 ppm (here designated "b") were used to calculate the relative concentration of butylamine in the mixture; the relative decrease in the concentration of the amine at a given time was calculated as a/(a+b). The time at which the amine and amide were equal in concentration was estimated to be 5.0 min. When compared to the aminolysis rate of the parent unsubstituted lactone, the relative half-life must be adjusted by dividing this time by a factor of 4 to compare rates since the reaction is approximately second order and the concentration was ½ of the concentration of the control. The half life was found to be 1.25 min.

Example 9

Aminolysis of 5,5'-[1,4-butylenebis(oxymethylene)]-bis[ethyl(tetrahydro-2-oxo)-3-furancarboxylate A solution of 5,5'-[1,4-butylenebis(oxymethylene)]-bis[ethyl(tetrahydro-2-oxo)-3-furancarboxylate (as prepared in Example 2) was prepared by weighing into a NMR tube 0.1883 g (0.0004375 mol) of 5,5'-[1,4-butylenebis(oxymethylene)]-bis[ethyl(tetrahydro-2-oxo)-3-furancarboxylate and 0.0291 g of durene dissolved in 0.441 g of DMF-d7. Then 0.086 ml (0.000875 mol) of N-butylamine was added. The tube was sealed and the $^1$H NMR spectrum recorded at various times. The integrated intensity of the triplet due to the methylene group adjacent to the nitrogen atom of butylamine at 2.58 ppm (here designated "a") and the integrated intensity of the triplet due to the methylene group adjacent to the amido nitrogen at 3.13 ppm (here designated "b") were used to calculate the relative concentration of butylamine in the mixture; the relative decrease in the concentration of the amine at a given time was calculated as a/(a+b). The half life was found to be 88 min.

Example 10

Aminolysis of 3-benzenesulfonyl-5-methyleneoxybutyl-butyrolactone

A solution of 3-benzenesulfonyl-5-methyleneoxybutyl-butyrolactone was prepared by weighing into a vial 0.1367 g (0.0004375 mol) of 3-benzenesulfonyl-5-methyleneoxybutyl-butyrolactone and 0.0145 g (0.000109 mol) of durene in 0.5418 g of CDCl$_3$. The solution was transferred to an NMR tube. The tube was cooled in an ice bath to 5° C. and then 0.043 ml (0.0004375 mol) of N-butylamine was added. The tube was sealed and the $^1$H NMR spectrum recorded at various times. The integrated intensity of the triplet due to the methylene group adjacent to the nitrogen atom of butylamine at 2.58 ppm (here designated "a") and the integrated intensity of the two multiplets at 4.6 and 4.75 ppm (here designated "b") were used to calculate the relative concentration of butylamine in the mixture; the relative decrease in the concentration of the amine at a given time was calculated as a/(a+b). The reaction of the lactone having the sulfonyl group was so rapid that the half life {a/(a+b)=0.5} had to be estimated from only a few data points. The time at which the amine and amide were equal in concentration was estimated to be 1.0 min. When compared to the aminolysis rate of the parent unsubstituted lactone, the relative half-life must be adjusted by dividing this time by a factor of 4 to compare rates since the reaction is approximately second order and the concentration was ½ of the concentration of the control.

Example 11

Aminolysis of 3,8-Dibutyl-2,7-dioxaspiro[4,4]nonane-1,6-dione

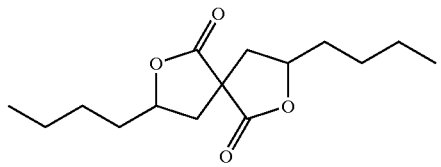

3,8-Dibutyl-2,7-dioxaspiro[4,4]nonane-1,6-dione was prepared according to W. E. Fristad and S. S. Hershberger, J. Org. Chem., 1985, 50(7), 1026–1031. Aminolysis of this lactone was followed by IR spectroscopy. The spiro lactone reacted rapidly in one ring and more slowly in the second ring.

Relative Aminolysis Rates of Unsubstituted and Substituted Gamma-Butyrolactones

Using the half-life for butyrolactone determined above (9926 min) and the aminolysis data given in Table 2 below, the relative aminolysis rates for the substituted gamma-butyrolactones can be calculated as described above. These rates are expressed as $\log(k/k_o)$, and are plotted versus the F value for the functional group at 21° C. as given in C. Hansch, et al., Chem. Rev., 1991, 91, pp. 165–195. This plot is shown in FIG. 1.

TABLE 1

| | Substituent | F[b] |
|---|---|---|
| 1 | BF$_2$ | 0.26 |
| 2 | Br | 0.45 |
| 3 | GeBr$_3$ | 0.61 |
| 4 | SiBr$_3$ | 0.44 |
| 5 | Cl | 0.42 |
| 6 | HgCl | 0.33 |
| 7 | SO$_2$Cl | 1.16 |
| 8 | SCl | 0.42 |
| 9 | ICl$_2$ | 1.03 |
| 10 | P(O)Cl$_2$ | 0.70 |
| 11 | PCl$_2$ | 0.50 |
| 12 | P(S)Cl$_2$ | 0.63 |
| 13 | GeCl$_3$ | 0.65 |
| 14 | SiCl$_3$ | 0.44 |
| 15 | F | 0.45 |
| 16 | HgF | 0.35 |
| 17 | SOF | 0.67 |
| 18 | SO$_2$F | 0.72 |
| 19 | IF$_2$ | 0.82 |
| 20 | POF$_2$ | 0.74 |
| 21 | PF$_2$ | 0.44 |
| 22 | GeF$_3$ | 0.76 |
| 23 | SF$_3$ | 0.63 |
| 24 | SiF$_3$ | 0.47 |
| 25 | IF$_4$ | 0.98 |
| 26 | PF$_4$ | 0.54 |
| 27 | SF$_5$ | 0.56 |
| 28 | I | 0.42 |
| 29 | IO | 0.55 |

TABLE 1-continued

| | Substituent | $F^b$ |
|---|---|---|
| 30 | $IO_2$ | 0.61 |
| 31 | NO | 0.49 |
| 32 | $NO_2$ | 0.65 |
| 33 | $ONO_2$ | 0.48 |
| 34 | $N{\equiv}N^+$ | 1.58 |
| 35 | $N{\equiv}N^+(BF_4)^-$ | 1.48 |
| 36 | $NNO_2^-$ | 0.20 |
| 37 | $N_3$ | 0.48 |
| 38 | $O^-$ | −0.26 |
| 39 | $SO_2^-$ | 0.03 |
| 40 | $SO_3^-$ | 0.29 |
| 41 | $S^-$ | 0.03 |
| 42 | $AsO_3H^-$ | 0.04 |
| 43 | H | 0.03 |
| 44 | $NHNO_2$ | 0.99 |
| 45 | OH | 0.33 |
| 46 | S(O)OH | 0.01 |
| 47 | $PO_3H^-$ | 0.19 |
| 48 | $OPO_3H^-$ | 0.41 |
| 49 | SH | 0.30 |
| 50 | $B(OH)_2$ | −0.03 |
| 51 | $NH_2$ | 0.08 |
| 52 | NHOH | 0.11 |
| 53 | $SO_2NH_2$ | 0.49 |
| 54 | $PO(OH)_2$ | 0.34 |
| 55 | $PH_2$ | 0.09 |
| 56 | $B(OH)_3^-$ | −0.42 |
| 57 | $GeH_3$ | 0.03 |
| 58 | $NH_3$ | 0.92 |
| 59 | $NHNH_2$ | 0.22 |
| 60 | $SiH_3$ | 0.06 |
| 61 | $CBr_3$ | 0.28 |
| 62 | $CClF_2$ | 0.40 |
| 63 | 5-chloro-1-tetrazolyl | 0.58 |
| 64 | CoCl | 0.46 |
| 65 | $N{=}CCl_2$ | 0.26 |
| 66 | $CCl_3$ | 0.38 |
| 67 | $OCCl_3$ | 0.46 |
| 68 | COF | 0.48 |
| 69 | $OCF_2O$ | 0.36 |
| 70 | $CF_3$ | 0.38 |
| 71 | $HgCF_3$ | 0.29 |
| 72 | $HgSCF_3$ | 0.38 |
| 73 | $I{=}NSO_2CF_3$ | 1.20 |
| 74 | $N{=}NCF_3$ | 0.50 |
| 75 | $OCF_3$ | 0.39 |
| 76 | $SOCF_3$ | 0.58 |
| 77 | $SeOCF_3$ | 0.76 |
| 78 | $SO_2CF_3$ | 0.74 |
| 79 | $SeO_2CF_3$ | 0.97 |
| 80 | $OSO_2CF_3$ | 0.56 |
| 81 | $SCF_3$ | 0.36 |
| 82 | $SeCF_3$ | 0.43 |
| 83 | HgCN | 0.27 |
| 84 | CN | 0.51 |
| 85 | NC | 0.47 |
| 86 | $CN(BBr_3)$ | 0.64 |
| 87 | $CN(BCl_3)$ | 0.93 |
| 88 | $CN(BF_3)$ | 0.71 |
| 89 | $N{=}C{=}O$ | 0.31 |
| 90 | OCN | 0.69 |
| 91 | $SO_2CN$ | 0.97 |
| 92 | $N{=}C{=}S$ | 0.51 |
| 93 | SCN | 0.49 |
| 94 | SeCN | 0.57 |
| 95 | $N{=}NCN$ | 0.56 |
| 96 | $N(O){=}NCN$ | 0.70 |
| 97 | $C(NO_2)_3$ | 0.65 |
| 98 | 5-azido-1-tetrazolyl | 0.53 |
| 99 | $CO_2^-$ | −0.10 |
| 100 | $CHBr_2$ | 0.31 |
| 101 | $CHCl_2$ | 0.31 |
| 102 | $OCHCl_2$ | 0.43 |
| 103 | $CHF_2$ | 0.29 |
| 104 | $OCHF_2$ | 0.37 |
| 105 | $SOCHF_2$ | 0.51 |
| 106 | $SO_2CHF_2$ | 0.67 |
| 107 | $SCHF_2$ | 0.32 |
| 108 | $S(O)({=}NH)CF_3$ | 0.64 |
| 109 | $NHSO_2CF_3$ | 0.45 |
| 110 | $CHI_2$ | 0.27 |
| 111 | NHCN | 0.28 |
| 112 | 1-(1H)-tetrazolyl | 0.52 |
| 113 | 5-(1H)-tetrazolyl | 0.65 |
| 114 | 5-hydroxy-1-tetrazolyl | 0.41 |
| 115 | 5-mercapto-1-tetrazolyl | 0.44 |
| 116 | ![structure: thiadiazolyl-HN] | 0.35 |
| 117 | CHO | 0.33 |
| 118 | COOH | 0.34 |
| 119 | $CH_2Br$ | 0.14 |
| 120 | $CH_2Cl$ | 0.13 |
| 121 | $OCH_2Cl$ | 0.33 |
| 122 | $CH_2F$ | 0.15 |
| 123 | $OCH_2F$ | 0.29 |
| 124 | $SCH_2F$ | 0.25 |
| 125 | $CH_2I$ | 0.12 |
| 126 | NHCHO | 0.28 |
| 127 | $CONH_2$ | 0.26 |
| 128 | $CSNH_2$ | 0.24 |
| 129 | $CH{=}NOH$-t | 0.28 |
| 130 | 3,4-N={CHNH}— | −0.10 |
| 131 | $N(O){=}NCONH_2$ | 0.56 |
| 132 | $OCH_2O$ | −0.11 |
| 133 | Me | 0.01 |
| 134 | $CH_2SO_2R$ | 0.16 |
| 135 | $SiMeCl_2$ | 0.29 |
| 136 | $SiMeF_2$ | 0.32 |
| 137 | HgMe | 0.55 |
| 138 | $NHCH_2SO_3^-$ | 0.12 |
| 139 | $NHCONH_2$ | 0.09 |
| 140 | $N(Me)NO_2$ | 0.43 |
| 141 | $NHCSNH_2$ | 0.26 |
| 142 | OMe | 0.29 |
| 143 | $CH_2OH$ | 0.03 |
| 144 | SOMe | 0.52 |
| 145 | S(OMe) | 0.24 |
| 146 | $OS({=}O)CH_3$ | 0.43 |
| 147 | S(O)OMe | 0.47 |
| 148 | $SO_2Me$ | 0.53 |
| 149 | $SSO_2Me$ | 0.38 |
| 150 | $OSO_2Me$ | 0.40 |
| 151 | SMe | 0.23 |
| 152 | SSMe | 0.27 |
| 153 | SeMe | 0.16 |
| 154 | NHMe | 0.03 |
| 155 | $CH_2NH_2$ | 0.04 |
| 156 | $NHSO_2Me$ | 0.28 |
| 157 | $CH_2NH_3^+$ | 0.59 |
| 158 | $N(COF)_2$ | 0.57 |
| 159 | $HgOCOCF_3$ | 0.48 |
| 160 | $COCF_3$ | 0.54 |
| 161 | $SCOCF_3$ | 0.48 |
| 162 | $OCOCF_3$ | 0.58 |
| 163 | $N(CF_3)C{=}O(F)$ | 0.49 |
| 164 | $CF_2OCF_2^-$ | 0.77 |
| 165 | $CF_2CF_3$ | 0.44 |
| 166 | $OCF_2CF_3$ | 0.55 |
| 167 | $SO_2CF_2CF_3$ | 0.81 |
| 168 | $SCF_2CF_3$ | 0.42 |
| 169 | $N(CF_3)_2$ | 0.35 |
| 170 | $S(CF_3){=}NSO_2CF_3$ | 1.07 |
| 171 | $SO(CF_3){-}NSO_2CF_3$ | 1.09 |
| 172 | $N(SO_2CF_3)_2$ | 0.50 |
| 173 | $P(CF_3)_2$ | 0.55 |
| 174 | $P(CN)_2$ | 0.75 |
| 175 | $C{\equiv}CH$ | 0.22 |

TABLE 1-continued

| | Substituent | $F^b$ |
|---|---|---|
| 176 | OCF$_2$CHCFCl | 0.38 |
| 177 | NHCOCF$_3$ | 0.38 |
| 178 | CH=NSO$_2$CF$_3$ | 0.63 |
| 179 | OCF$_2$CHF$_2$ | 0.38 |
| 180 | SCF$_2$CHF$_2$ | 0.35 |
| 181 | (structure: bis-tetrazolyl sulfide) | 0.60 |
| 182 | SC≡CH | 0.30 |
| 183 | SCH=CHCl | 0.34 |
| 184 | SeCH=CHCl | 0.30 |
| 185 | CH$_2$CF$_3$ | 0.15 |
| 186 | CH$_2$SOCF$_3$ | 0.27 |
| 187 | CH$_2$SO$_2$CF$_3$ | 0.29 |
| 188 | CH$_2$SCF$_3$ | 0.13 |
| 189 | CH$_2$CN | 0.17 |
| 190 | CH=CHNO$_2$-t | 0.35 |
| 191 | CH$_2$CO$_2^-$ | 0.19 |
| 192 | CH$_2$SCN | 0.14 |
| 193 | CH=CH$_2$ | 0.13 |
| 194 | NHCOCH$_2$Cl | 0.27 |
| 195 | N(Me)SO$_2$CF$_3$ | 0.46 |
| 196 | HgOCOCH$_3$ | 0.39 |
| 197 | C(Me)(NO$_2$)$_2$ | 0.50 |
| 198 | oxiranyl | 0.09 |
| 199 | OCH=CH$_2$ | 0.34 |
| 200 | COMe | 0.33 |
| 201 | SCOMe | 0.37 |
| 202 | OCOMe | 0.42 |
| 203 | COOMe | 0.34 |
| 204 | 2-thiacyclopropyl | 0.08 |
| 205 | SCH=CH$_2$ | 0.29 |
| 206 | SeCH=CH$_2$ | 0.29 |
| 207 | 1-aziridinyl | 0.03 |
| 208 | 2-aziridinyl | −0.01 |
| 209 | N-methyl-3-oxaziridinyl | 0.10 |
| 210 | NHCOOMe | 0.07 |
| 211 | NHCOMe | 0.31 |
| 212 | CONHMe | 0.35 |
| 213 | CH=NOMe | 0.40 |
| 214 | CH$_2$CONH$_2$ | 0.08 |
| 215 | NHCSMe | 0.30 |
| 216 | CSNHMe | 0.29 |
| 217 | CH=NNHSCNH$_2$ | 0.46 |
| 218 | OCH$_2$CH$_2$O$^-$ | −0.08 |
| 219 | Et | 0.00 |
| 220 | CH=NNHCONHNH$_2$ | 0.26 |
| 221 | OCH$_2$CH$_3$ | 0.26 |
| 222 | CH(OH)Me | 0.16 |
| 223 | CH$_2$OMe | 0.13 |
| 224 | SO$_2$Et | 0.59 |
| 225 | SEt | 0.26 |
| 226 | P(Cl)NMe$_2$ | 0.31 |
| 227 | CH$_2$SC(NH$_2$)$_2{}^+$ | 0.14 |
| 228 | SiClMe$_2$ | 0.16 |
| 229 | SiFMe$_2$ | 0.12 |
| 230 | NHEt | −0.04 |
| 231 | N(Me)$_2$ | 0.15 |
| 232 | N(Me)SO$_2$Me | 0.21 |
| 233 | SO$_2$NMe$_2$ | 0.44 |
| 234 | N(SO$_2$Me)$_2$ | 0.45 |
| 235 | SN(Me)$_2$ | 0.15 |
| 236 | N=NNMe$_2$ | −0.02 |
| 237 | N(Me)N$^+$=(Me)N— | 1.10 |
| 238 | P(O)Me$_2$ | 0.40 |
| 239 | PO(OMe)$_2$ | 0.37 |
| 240 | PMe$_2$ | 0.05 |
| 241 | S$^+$Me$_2$ | 0.98 |
| 242 | S$^+$(Me)$_2$tosyl | 1.04 |
| 243 | CH$_2$CH$_2$NH$_3{}^+$ | 0.27 |
| 244 | SiH(Me)$_2$ | 0.03 |
| 245 | 1-(1,7(BH)$_{10}$—C$_2$H) | 0.23 |
| 246 | 2-(1,7(BH)$_{10}$—C$_2$H) | 0.16 |
| 247 | 4-(1,7(BH)$_{10}$—C$_2$H) | 0.00 |
| 248 | 1-(1,2(BH)$_{10}$—C$_2$H) | 0.50 |
| 249 | 3-(1,2(BH)$_{10}$—C$_2$H) | 0.22 |
| 250 | C≡CCF$_3$ | 0.37 |
| 251 | CF=CFCF$_3$-t | 0.36 |
| 252 | N=C(CF$_3$)$_2$ | 0.32 |
| 253 | CF$_2$CF$_2$CF$_3$ | 0.42 |
| 254 | CF(CF$_3$)$_2$ | 0.31 |
| 255 | SO$_2$CF$_2$CF$_2$CF$_3$ | 0.81 |
| 256 | SO$_2$CF(CF$_3$)$_2$ | 0.80 |
| 257 | SCF$_2$CF$_2$CF$_3$ | 0.43 |
| 258 | SCF(CF$_3$)$_2$ | 0.46 |
| 259 | TeCF$_2$CF$_2$CF$_3$ | 0.45 |
| 260 | C(OH)(CF$_3$)$_2$ | 0.29 |
| 261 | CH(SCF$_3$)$_2$ | 0.43 |
| 262 | CH(CN)$_2$ | 0.52 |
| 263 | CH=CHCF$_3$-c | 0.18 |
| 264 | CH=CHCF$_3$-t | 0.24 |
| 265 | CH=CHSO$_2$CF$_3$ | 0.22 |
| 266 | CH=CHCN | 0.28 |
| 267 | C≡CMe | 0.29 |
| 268 | N(Me)COCF$_3$ | 0.41 |
| 269 | CH=CHCHO | 0.29 |
| 270 | cyclopropyl | 0.02 |
| 271 | C(Me)=CH$_2$ | 0.13 |
| 272 | CH=CHMe-t | 0.09 |
| 273 | CH$_2$CH=CH$_2$ | −0.06 |
| 274 | C(Et)(NO$_2$)$_2$ | 0.51 |
| 275 | OCH$_2$CH=CH$_2$ | 0.25 |
| 276 | COEt | 0.34 |
| 277 | COOEt | 0.34 |
| 278 | CH$_2$OCOMe | 0.07 |
| 279 | CH$_2$CH$_2$COOH | 0.02 |
| 280 | SCH$_2$CH=CH$_2$ | 0.23 |
| 281 | SeCH$_2$CH=CH$_2$ | 0.26 |
| 282 | CH$_2$CH$_2$CH$_2$— | −0.20 |
| 283 | N(Me)COMe | 0.34 |
| 284 | CH$_2$NHCOMe | 0.12 |
| 285 | NHCOOEt | 0.23 |
| 286 | C(NO$_2$)Me$_2$ | 0.19 |
| 287 | OCH$_2$CH$_2$CH$_2$O— | 0.03 |
| 288 | isopropyl | 0.04 |
| 289 | CH$_2$CH$_2$CH$_3$ | 0.01 |
| 290 | N$^+$(Me)=CHN(Me)— | 1.05 |
| 291 | NHCONHEt | 0.19 |
| 292 | NHCSNHEt | 0.40 |
| 293 | OCHMe$_2$ | 0.34 |
| 294 | OCH$_2$CH$_2$CH$_3$ | 0.26 |
| 295 | CH$_3$CH(OH)Me | −0.06 |
| 296 | C(OOH)Me$_2$ | 0.17 |
| 297 | SCHMe$_2$ | 0.30 |
| 298 | CH$_2$NMe$_2$ | 0.03 |
| 299 | GeMe$_3$ | 0.03 |
| 300 | N$^+$(Me)$_3$ | 0.86 |
| 301 | CH$_2$NH$^+$(Me)$_2$ | 0.39 |
| 302 | Si(Me)$_2$OMe | 0.09 |
| 303 | OSiMe$_3$ | 0.31 |
| 304 | SiMe(OMe)$_2$ | 0.05 |
| 305 | Si(OMe)$_3$ | 0.10 |
| 306 | P$^+$Me$_3$ | 0.71 |
| 307 | SiMe$_3$ | 0.01 |
| 308 | SnMe$_3$ | 0.03 |
| 309 | 1-(1,2-(BH)$_{10}$—C$_2$Me) | 0.43 |
| 310 | CH$_2$-1-(1,7-(BH)$_{10}$—C$_2$H) | 0.03 |
| 311 | CH$_2$-1-(1,2-(BH)$_{10}$—C$_2$H) | 0.14 |
| 312 | 1-(1,2)-(BH)$_{10}$—C$_3$H$_3$HgCH$_3$) | 0.82 |
| 313 | 2-(hydroxymethyl)carboran-1-yl | 0.34 |
| 314 | I(OCOCF$_3$)$_2$ | 1.18 |
| 315 | cyclo-C$_4$F$_7$ | 0.45 |
| 316 | COCF$_2$CF$_2$CF$_3$ | 0.55 |
| 317 | C(CF$_3$)$_3$ | 0.53 |
| 318 | (CF$_2$)$_3$CF$_3$ | 0.44 |
| 319 | SO$_2$C(CF$_3$)$_3$ | 0.84 |
| 320 | SC(CF$_3$)$_3$ | 0.47 |

TABLE 1-continued

| | Substituent | F[b] |
|---|---|---|
| 321 | C(SCF$_3$)$_3$ | 0.49 |
| 322 | SeC(CF$_3$)$_3$ | 0.46 |
| 323 | C(CN)$_3$ | 0.92 |
| 324 | cyclo-1-(OH)C$_4$F$_6$ | 0.36 |
| 325 | CH=C(CN)$_2$ | 0.57 |
| 326 | 2-(5-bromofuryl) | 0.23 |
| 327 | (3-chloro=1-pyrroline-2,5-dione structure) | 0.36 |
| 328 | 3-chloro=1-pyrroline-2,5-dione | 0.47 |
| 329 | 3-pyridazinyl | 0.21 |
| 330 | 3,4-CH=CHCH—CH— | 0.07 |
| 331 | C(Me)(CN)$_2$ | 0.59 |
| 332 | 4-pyrimidinyl | 0.18 |
| 333 | 2-pyrimidinyl | 0.13 |
| 334 | 5-pyrimidinyl | 0.25 |
| 335 | 2-furyl | 0.10 |
| 336 | 2-thienyl | 0.13 |
| 337 | 3-thienyl | 0.08 |
| 338 | 2-selenienyl | 0.10 |
| 339 | 2-tellurienyl | 0.10 |
| 340 | 1-pyrryl | 0.50 |
| 341 | 1-pyrroline-2,5-dione | 0.36 |
| 342 | CH=CHCOMe | 0.31 |
| 343 | I(OCOMe)$_2$ | 0.80 |
| 344 | N(COMe)$_2$ | 0.36 |
| 345 | cyclobutyl | 0.02 |
| 346 | COCHMe$_2$ | 0.35 |
| 347 | (CH$_2$)$_4$ | −0.40 |
| 348 | NHCOCH(Me)$_2$ | 0.21 |
| 349 | C(Me)$_3$ | −0.02 |
| 350 | CH(Me)Et | −0.02 |
| 351 | CH$_2$CH(Me)$_2$ | −0.01 |
| 352 | (CH$_2$)$_3$CH$_3$ | −0.01 |
| 353 | O(CH$_2$)$_3$CH$_3$ | 0.29 |
| 354 | CH$_2$C(OH)Me$_2$ | −0.11 |
| 355 | C(OMe)$_3$ | 0.01 |
| 356 | AsEt$_2$ | 0.32 |
| 357 | As(O)Et$_2$ | 0.60 |
| 358 | As(S)Et$_2$ | 0.54 |
| 359 | NH(CH$_2$)$_3$CH$_3$ | −0.21 |
| 360 | N(Et)$_2$ | 0.01 |
| 361 | PO(Et)$_2$ | 0.33 |
| 362 | N=NPO(OEt)$_2$ | 0.05 |
| 363 | PO(OEt)$_2$ | 0.52 |
| 364 | P(Et)$_2$ | 0.11 |
| 365 | P(S)Et$_2$ | 0.36 |
| 366 | CH$_2$N(Me)$_3^+$ | 0.38 |
| 367 | CH$_2$CH$_2$NH(Me)$_2^+$ | 0.29 |
| 368 | CH$_2$OSi(CH$_3$)$_3$ | 0.00 |
| 369 | CH$_2$Si(Me)$_3$ | −0.09 |
| 370 | PO(N(Me)$_2$)$_2$ | 0.27 |
| 371 | P(N(Me)$_2$)$_2$ | 0.17 |
| 372 | 2-(methylcarbonyl)carboran-1-yl | 0.31 |
| 373 | 2-[(carbonyloxy)methyl]carboran-1-yl | 0.66 |
| 374 | CH$_2$-1-(1,2-(BH)$_{10}$—C$_2$Me) | 0.12 |
| 375 | C(CN)=C(CN)$_2$ | 0.65 |
| 376 | 2-(5-cyanofuryl) | 0.32 |
| 377 | 2-(5-formylfuryl) | 0.34 |
| 378 | 2-pyridyl | 0.40 |
| 379 | 3-pyridyl | 0.24 |
| 380 | 4-pyridyl | 0.21 |
| 381 | 2-(4,6-dimethyl-s-triazinyl) | 0.21 |
| 382 | 1-cyclopentenyl | −0.03 |
| 383 | CH=CHCOOEt | 0.27 |
| 384 | cyclopentyl | 0.02 |
| 385 | COC(Me)$_3$ | 0.26 |
| 386 | NHCO$_2$(CH$_2$)$_3$CH$_3$ | 0.13 |
| 387 | C(Et)(Me)$_2$ | 0.03 |
| 388 | CH$_2$C(Me)$_3$ | 0.03 |
| 389 | (CH$_2$)$_4$CH$_3$ | −0.01 |
| 390 | O(CH$_2$)$_4$CH$_3$ | 0.29 |
| 391 | CH$_2$PO(OEt)$_2$ | 0.17 |
| 392 | CH$_2$CH$_2$N(Me)$_3^+$ | 0.19 |
| 393 | CH$_2$CH$_2$Si(Me)$_3$ | −0.11 |
| 394 | Si(Me)$_2$OSi(Me)$_3$ | 0.04 |
| 395 | C$_6$Cl$_5$ | 0.27 |
| 396 | C$_6$F$_5$ | 0.27 |
| 397 | P(O)(C$_3$F$_7$)$_2$ | 0.84 |
| 398 | OP(O)(C$_3$F$_7$)$_2$ | 0.67 |
| 399 | NHP(O)(C$_3$F$_7$)$_2$ | 0.33 |
| 400 | CH$_2$Co(CN)$_5^{-3}$ | −0.39 |
| 401 | CH$_2$Mn(CO)$_5$ | 0.02 |
| 402 | C$_6$H$_2$-2,4,6-(NO$_2$)$_3$ | 0.26 |
| 403 | C$_6$H$_4$-3-Br | 0.12 |
| 404 | C$_6$H$_4$-4-Br | 0.18 |
| 405 | C$_6$H$_4$-3-Cl | 0.19 |
| 406 | C$_6$H$_4$-4-Cl | 0.18 |
| 407 | C$_6$H$_4$-3-F | 0.19 |
| 408 | C$_6$H$_4$-4-F | 0.17 |
| 409 | OC$_6$H$_4$-4-F | −0.03 |
| 410 | C$_6$H$_4$-3-I | 0.18 |
| 411 | C$_6$H$_4$-4-I | 0.18 |
| 412 | C$_6$H$_4$-3-NO$_2$ | 0.23 |
| 413 | C$_6$H$_4$-4-NO$_2$ | 0.26 |
| 414 | SC$_6$H$_4$-4-NO$_2$ | 0.36 |
| 415 | SOC$_6$H$_4$-4-NO$_2$ | 0.55 |
| 416 | 2-benzotriazolyl | 0.47 |
| 417 | C$_6$H$_5$ | 0.12 |
| 418 | N(O)=NSO$_2$C$_6$H$_5$ | 0.62 |
| 419 | N=NC$_6$H$_5$ | 0.30 |
| 420 | OC$_6$H$_5$ | 0.37 |
| 421 | SOC$_6$H$_5$ | 0.51 |
| 422 | 2-(5-acetylfuryl) | 0.31 |
| 423 | 2-(6-methylpyronyl) | 0.36 |
| 424 | SO$_2$C$_6$H$_5$ | 0.58 |
| 425 | OSO$_2$C$_6$H$_5$ | 0.37 |
| 426 | SC$_6$H$_5$ | 0.30 |
| 427 | NHC$_6$H$_5$ | 0.22 |
| 428 | HNSO$_2$C$_6$H$_5$ | 0.24 |
| 429 | SO$_2$NHC$_6$H$_5$ | 0.51 |
| 430 | 2-(5-ethylfuryl) | 0.20 |
| 431 | 1-(2,5-dimethylpyrryl) | 0.52 |
| 432 | 1-cyclohexenyl | −0.07 |
| 433 | cyclohexyl | 0.03 |
| 434 | N(C$_3$H$_7$)$_2$ | 0.06 |
| 435 | (CH$_2$)$_4$NMe$_2$ | −0.01 |
| 436 | PO(isopropyl)$_2$ | 0.36 |
| 437 | P(isopropyl)$_2$ | 0.04 |
| 438 | P(O)(OPr)$_2$ | 0.33 |
| 439 | Ge(Et)$_3$ | 0.03 |
| 440 | (CH$_2$)$_3$N(Me)$_3^+$ | 0.12 |
| 441 | Si(OEt)$_3$ | 0.03 |
| 442 | P(Et)$_3^+$ | 0.94 |
| 443 | Sn(Et)$_3$ | 0.03 |
| 444 | P(=NSO$_2$CF$_3$)(C$_3$F$_7$)$_2$ | 1.11 |
| 445 | Si(NMe$_2$)$_3$ | 0.00 |
| 446 | 2-benzoxazolyl | 0.30 |
| 447 | 2-benzthiazolyl | 0.27 |
| 448 | COC$_6$H$_5$ | 0.31 |
| 449 | OCOC$_6$H$_5$ | 0.26 |
| 450 | COOC$_6$H$_5$ | 0.34 |
| 451 | N=CHC$_6$H$_5$ | 0.14 |
| 452 | CH=NC$_6$H$_5$ | 0.33 |
| 453 | NHCOC$_6$H$_5$ | 0.13 |
| 454 | CONHC$_6$H$_5$ | 0.17 |
| 455 | C$_6$H$_5$-4-Me | 0.12 |
| 456 | CH$_2$C$_6$H$_5$ | −0.04 |
| 457 | N=NC$_6$H$_3$-5-Me-2-OH | 0.26 |
| 458 | C$_6$H$_4$-4-OMe | 0.13 |
| 459 | CH(OH)C$_6$H$_5$ | 0.05 |
| 460 | CH$_2$OC$_6$H$_5$ | 0.08 |
| 461 | CH$_2$SO$_2$C$_6$H$_5$ | 0.17 |
| 462 | C(Et)$_3$ | 0.02 |
| 463 | (CH$_2$)$_6$CH$_3$ | 0.00 |
| 464 | SiMe(OSi(Me)$_3$)$_2$ | 0.01 |

TABLE 1-continued

| | Substituent | $F^b$ |
|---|---|---|
| 465 | $CF_2CF_2C_6H_4$-4-F | 0.32 |
| 466 | $C\equiv CC_6H_5$ | 0.15 |
| 467 | $CH=NCOC_6H_5$ | 0.34 |
| 468 | $CH=CHC_6H_5$ | 0.10 |
| 469 | $CH_2Fe(CO)_2(\chi\text{-}C_5H_5)$ | −0.11 |
| 470 | $CH=NNHCOC_6H_5$ | 0.34 |
| 471 | $N=CHC_6H_4$-4-OMe | 0.15 |
| 472 | $NHCOC_6H_4$-4-OMe | 0.17 |
| 473 | $SCH=NSO_2C_6H_4$-4-Me | 0.61 |
| 474 | $C_6H_4$-4-Et | 0.13 |
| 475 | $CH_2CH_2C_6H_5$ | −0.01 |
| 476 | $N=C(Me)NHC_6H_5$ | 0.38 |
| 477 | $Si(C_6H_5)(Me)_2$ | 0.06 |
| 478 | $S(Me)=NSO_2C_6H_4$-4-Me | 0.61 |
| 479 | 2,4,6-trimethylpyridinium | 0.61 |
| 480 | $PO(CMe_3)_2$ | 0.28 |
| 481 | $PO(C_4H_9)_2$ | 0.30 |
| 482 | $PO(OC_4H_9)_2$ | 0.35 |
| 483 | $P(CMe_3)_2$ | −0.01 |
| 484 | $C_6H_5Cr(CO)_3$ | 0.36 |
| 485 | 2-benzo-4-thiopyronyl | 0.34 |
| 486 | 2-(benzothiopyronyl) | 0.48 |
| 487 | 2-(benzo-1,4-pyronyl) | 0.41 |
| 488 | $CH=CHCOC_6H_4$-4-$NO_2$ | 0.21 |
| 489 | $CH_2Mo(CO)_3(C_5H_5)$ | −0.07 |
| 490 | $CH=CHCOC_6H_5$ | 0.25 |
| 491 | $C_6H_4$-4-$CHMe_2$ | 0.13 |
| 492 | $Si(OSiMe_3)_3$ | −0.08 |
| 493 | ferrocenyl | −0.09 |
| 494 | ferricenium$^+$ | 0.30 |
| 495 | ferrocenonium$^+$ | −0.01 |
| 496 | $C_6H_4$-4-$CMe_3$ | 0.12 |
| 497 | 1-adamantyl | −0.07 |
| 498 | 1-dibenzarsenyl | 0.23 |
| 499 | 1-dibenzoarsoxyl | 0.22 |
| 500 | 1-dibenzoarsazinyl | 0.18 |
| 501 | $As(C_6H_5)_2$ | 0.04 |
| 502 | $AsO(C_6H_5)_2$ | 0.49 |
| 503 | $P(C_6H_5)_2(BCl_3)$ | 0.62 |
| 504 | $N(C_6H_5)_2$ | 0.12 |
| 505 | $PO(C_6H_5)_2$ | 0.32 |
| 506 | $P(C_6H_5)_2$ | 0.10 |
| 507 | $PS(C_6H_5)_2$ | 0.22 |
| 508 | $P(N(C_3H_7)_2)C_6H_4$-3-F | 0.20 |
| 509 | [2-methyl-4H-naphtho[2,1-b]pyran-4-one structure] | 0.37 |
| 510 | [3-methyl-1H-naphtho[2,1-b]pyran-1-one structure] | 0.38 |
| 511 | [1-phenyl-2-methylbenzimidazole structure] | 0.17 |
| 512 | $CH(C_6H_5)_2$ | 0.01 |
| 513 | [10-methyl-5-arsa-phenazine structure] | 0.16 |
| 514 | $PO(C_6H_5)C_6H_4$-4-Me | 0.09 |
| 515 | $CH_2PO(C_6H_5)_2$ | 0.21 |
| 516 | $PS(C_6H_5)C_6H_4$-4-Me | 0.03 |
| 517 | $P^+(Me)(C_6H_5)_2$ | 1.04 |
| 518 | $Si(Me)(C_6H_5)_2$ | 0.11 |
| 519 | $COOCH(C_6H_5)_2$ | 0.28 |
| 520 | $PO(C_6H_4$-4-Me$)_2$ | 0.14 |
| 521 | $PS(C_6H_4$-4-Me$)_2$ | 0.20 |
| 522 | $P^+(Me)(C_6H_5)(C_6H_4$-4-Me$)$ | 1.02 |
| 523 | $P^+(Me)(C_6H_4$-4-Me$)_2$ | 1.04 |
| 524 | $Ge(C_6H_5)_3$ | 0.07 |
| 525 | 2-methyl-4,6-diphenylpyridinium | 0.61 |
| 526 | $N=P(C_6H_5)_3$ | −0.10 |
| 527 | $Si(C_6H_5)_3$ | −0.04 |
| 528 | $Sn(C_6H_5)_3$ | (0.62) |
| 529 | $C(C_6H_5)_3$ | 0.01 |
| 530 | 2,4,6-triphenylpyridinium | 0.35 |

TABLE 2

Kinetic Values and Reaction Rates for Unsubstituted and Substituted Gamma-Butyrolactones

| Ex. No. | Func. Group | F Value | Equiv. Lactone and $BuNH_2$ | Obs. Crossover time (min.) | Kinetic Correction Factor | Corrected $t_{1/2}$ (min) | Log $(k/k_o)$ |
|---|---|---|---|---|---|---|---|
| 1 | CN | 0.51 | 0.000437 | 5 | ¼ | 1.25 | 3.90 |
| 3 | $SO_2$phenyl | 0.58 | 0.000437 | 1 | ¼ | 0.25 | 4.60 |

TABLE 2-continued

Kinetic Values and Reaction Rates for Unsubstituted and Substituted Gamma-Butyrolactones

| Ex. No. | Func. Group | F Value | Equiv. Lactone and BuNH$_2$ | Obs. Crossover time (min.) | Kinetic Correction Factor | Corrected $t_{1/2}$ (min) | Log (k/k$_o$) |
|---|---|---|---|---|---|---|---|
| Parent | H | 0.03 | 0.000875 | 9926 | 1 | 9926 | 0 |
| 2 | CO$_2$Et | 0.34 | 0.000875 | 88 | 1 | 88 | 2.05 |

What is claimed is:

1. A lactone composition having the structural formula I, wherein each n is independently 1 to 3;

L is either present as a substituent having two functional groups, or is a direct bond forming a spiro-bislactone, or is H wherein rings of the structure I are not connected, or is a radically polymerizable group wherein the rings of the structure I are not connected;

wherein Y is either present independently as alkyl, alkenyl, alkynyl, or aryl or is a direct bond;

each X is independently a substituent having a field effect, F, between −0.42 and +1.58

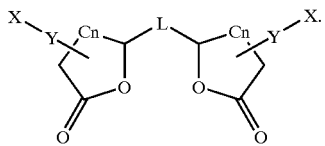

wherein said lactone is employed as a cross-linking agent in a coating composition containing amine compound (s) that are reactive with lactone groups.

2. The lactone of claim 1 wherein when Y is alkenyl, the alkenyl group is defined as

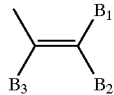

wherein $B_1$, $B_2$, and $B_3$ are individually a substituent group X as defined in claim 1.

3. A lactone of claim 1 wherein when Y is phenyl, the phenyl group is defined as

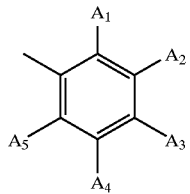

wherein $A_1$, $A_2$, $A_3$, $A_4$, and $A_5$ are each independently a substituent group X as defined in claim 1.

4. A composition of claim 1 wherein the L substituent having two functional groups is

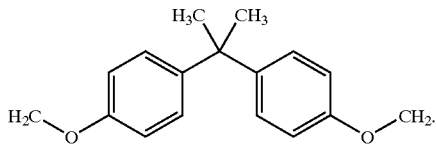

5. A composition of claim 1 wherein the L substituent having two functional groups is

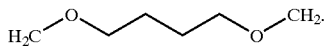

6. A composition of claim 1 wherein X is selected from the group consisting of and identified with the numbers 2, 5, 15, 28, 30, 32, 33, 34, 35, 37, 40, 43, 45, 47, 48, 49, 58, 62, 70, 74, 75, 76, 77, 78, 80, 84, 85, 90, 93, 94, 95, 97, 98, 99, 100, 101, 102, 103, 111, 112, 113, 114, 115, 116, 117, 118, 119, 120, 122, 125, 127, 128, 133, 139, 141, 142, 143, 144, 148, 150, 151, 153, 156, 160, 161, 162, 163, 165, 166, 167, 168, 169, 175, 177, 178, 179, 185, 186, 187, 188, 189, 191, 192, 193, 194, 195, 197, 198, 199.200, 201, 202, 203, 204, 205, 206, 207, 208, 209, 210, 211, 212, 213, 214, 215, 216, 217, 219, 221, 222, 223, 224, 225, 231, 232, 233, 234, 238, 239, 240, 241, 242, 243, 244, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 283, 284, 285, 286, 288, 289, 291, 292, 293, 294, 295, 297, 298, 300, 301, 302, 303, 304, 305, 306, 307, 308, 314, 315, 316, 317, 318, 319, 320, 321, 322, 323, 324, 325, 326, 327, 328, 329, 331, 332, 333, 334, 335, 336, 337, 338, 339, 340, 341, 342, 343, 344, 345, 346, 348, 349, 350, 351, 352, 353, 354, 355, 356, 357, 358, 359, 360, 361, 362, 363, 364, 365, 366, 367, 368, 369, 370, 371, 375, 376, 377, 378, 379, 380, 381, 382, 383, 384, 385, 386, 387, 388, 389, 390, 391, 392, 393, 394, 395, 396, 397, 398, 399, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 453, 454, 455, 456, 457, 458, 459, 460, 461, 462, 463, 464, 465, 466, 467, 468, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510 511, 512, 513, 514, 515, 516, 517, 518, 519, 520, 521, 522, 523, 524, 525, 526, 527, 528, 529 and 530 in Table 1.

7. A composition of claim 1 wherein X is selected from the group consisting of and identified with the numbers 2, 5, 15, 28, 32, 33, 40, 45, 49, 70, 75, 76, 78, 80, 84, 85, 90, 93, 99, 100, 101, 102, 103, 111, 117, 118, 119, 120, 122, 125, 127, 128, 133, 139, 141, 142, 143, 144, 148, 150, 151, 153, 156, 160, 161, 162, 165, 166, 167, 168, 169, 175, 177, 178, 179, 185, 186, 187, 188, 189, 191, 192, 193, 194, 194, 198, 199, 200, 201, 202, 203, 207, 210, 211, 212, 213, 214, 215, 216, 217, 219, 221, 222, 223, 224, 225, 231, 232, 233, 234, 238, 239, 240, 241, 250, 251, 252, 253, 254, 267, 270, 271, 272, 273, 275, 276, 277, 278, 279, 285, 291, 292, 293, 294, 295, 297, 298, 300, 303, 317, 318, 323, 325, 332, 333, 334, 335, 336, 337, 345, 378, 379, 380, 384, 388, 395, 396, 403, 404, 405, 406, 407, 408, 409, 410, 411, 416, 417, 420, 424, 425, 433, 448, 449, 450, 453, 458, 460, 474, 475 and 512 in Table 1.

8. A process comprising: contacting lactones of structure B with an amine to form a hydroxy amide, wherein each Y is present independently as alkyl, alkenyl, alkynyl, aryl, or a direct bond to X; each X is independently a substituent having a field effect, F, between −0.42 and +1.58; wherein R is a branched or straight chain alkyl group of $C_1$ to $C_{10}$, or an aryl group; and wherein each n is independently 1 to 3

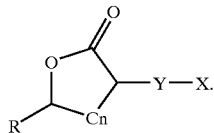
"B"

9. A process comprising: contacting a spiro-bislactone of structure A, wherein each n=1 to 3 independently and R is a branched or straight chain alkyl group of $C_1$ to $C_{10}$, or an aryl group; and wherein each n is independently 1 to 3; with an amine to form a hydroxy amide

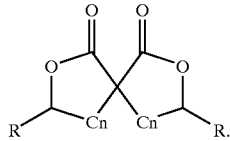
"A"

10. A process comprising: contacting a bicyclo-lactone of structure C wherein R is a branched or straight chain alkyl group of $C_1$ to $C_{10}$, or an aryl group, or C(O)OE wherein E is independently alkyl or aryl, with a amine

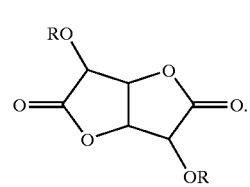
"C"

11. A process comprising: contacting a polymer containing one or more lactone groups prepared from at least one lactone monomer of structure D with an amine to form a hydroxy amide, wherein each Y is present independently as alkyl, alkenyl, alkynyl, aryl, or a direct bond to X; each X is independently a substituent having a field effect, F, between −0.42 and +1.58; wherein $R_{PG}$ is a radically polymerizable substituent group selected from the group consisting of styrene, acrylate, methacrylate, acrylamide, and methacrylamide; and wherein each n is independently 1 to 3

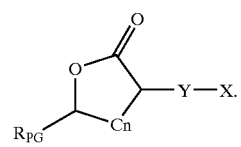
"D"

12. A process, comprising:
(i) performing the steps of any one of the claims 8, 9, 10 or 11;
(ii) applying a product resulting from step (i) to an object surface.

13. An article treated by the process of claim 12.

* * * * *